United States Patent
Schuster et al.

(10) Patent No.: US 10,126,286 B2
(45) Date of Patent: Nov. 13, 2018

(54) LANCE AND METHOD FOR DETERMINING REACTION DATA OF THE COURSE OF A REACTION

(71) Applicant: VOESTALPINE STAHL GMBH, Linz (AT)

(72) Inventors: Stefan Schuster, Enns (AT); Gunter Lengauer, Gallneukirchen (AT); Harald Panhofer, Linz (AT)

(73) Assignee: VOESTALPINE STAHL GMBH, Linz (AT)

(*) Notice: Subject to any disclaimer, the term of this patent is extended or adjusted under 35 U.S.C. 154(b) by 0 days.

(21) Appl. No.: 15/613,417

(22) Filed: Jun. 5, 2017

(65) Prior Publication Data
US 2017/0269050 A1 Sep. 21, 2017

Related U.S. Application Data

(62) Division of application No. 14/779,615, filed as application No. PCT/AT2014/050074 on Mar. 25, 2014.

(30) Foreign Application Priority Data

Mar. 25, 2013 (AT) .............................. A 50204/2013

(51) Int. Cl.
*G01N 33/00* (2006.01)
*G01N 33/20* (2006.01)
(Continued)

(52) U.S. Cl.
CPC ......... *G01N 33/206* (2013.01); *C21C 5/4606* (2013.01); *C21C 5/4673* (2013.01);
(Continued)

(58) Field of Classification Search
CPC .......... G01N 7/00; G01N 35/00; G01N 33/00; G01N 33/20
(Continued)

(56) References Cited

U.S. PATENT DOCUMENTS

| | | | |
|---|---|---|---|
| 3,045,997 | A | 7/1962 | Hudson |
| 3,378,366 | A | 4/1968 | Borowski et al. |
| 3,780,581 | A | 12/1973 | Acre et al. |
| 4,192,490 | A | 3/1980 | Nilsson et al. |
| 4,359,211 | A | 11/1982 | Baumert |
| 4,406,443 | A | 9/1983 | Moriyama |

(Continued)

FOREIGN PATENT DOCUMENTS

| | | |
|---|---|---|
| DE | 1 290 557 B | 3/1969 |
| DE | 2 239 216 A1 | 5/1973 |

(Continued)

OTHER PUBLICATIONS

International Search Report of PCT/AT2014/050074, dated Oct. 13, 2014.

*Primary Examiner* — Brian J. Sines
(74) *Attorney, Agent, or Firm* — Collard & Roe, P.C.

(57) ABSTRACT

A lance and a method determine reaction data of the course of a reaction, in which a reaction gas is top-blown by at least one lance onto a metallic melt in a metallurgical vessel and measured data are determined in this way, reaction data for the course of the reaction are determined as a function of these, where the lance for determining measured data blows out a gas which is conveyed separately from the reaction gas through at least one outlet opening of at least one measuring conduit. The lance for determining measured data blows out the gas which is conveyed separately from the reaction gas laterally through at least one outlet opening of at least one measuring conduit and the internal pressure of at least one gas bubble of this gas formed at this outlet opening of the respective measuring conduit is measured.

8 Claims, 2 Drawing Sheets

(51) Int. Cl.
*C21C 5/46* (2006.01)
*F27D 3/16* (2006.01)
*F27D 19/00* (2006.01)
*G01N 7/18* (2006.01)

(52) U.S. Cl.
CPC ............... *F27D 3/16* (2013.01); *F27D 19/00* (2013.01); *G01N 7/18* (2013.01); *F27D 2003/164* (2013.01); *F27D 2003/166* (2013.01); *F27D 2003/167* (2013.01); *F27D 2003/168* (2013.01)

(58) Field of Classification Search
USPC ..... 436/43, 148, 2, 34, 47, 73, 87; 700/266; 702/1, 22, 23, 30; 422/50, 129
See application file for complete search history.

(56) References Cited

U.S. PATENT DOCUMENTS

| | | |
|---|---|---|
| 4,602,574 A | 7/1986 | Bach et al. |
| 4,750,716 A | 6/1988 | Reeve-Parker |
| 4,854,553 A | 8/1989 | Labate |
| 5,244,646 A | 9/1993 | Stanley |
| 5,282,881 A | 2/1994 | Baldock et al. |
| 5,443,572 A | 8/1995 | Wilkinson et al. |
| 5,571,486 A | 11/1996 | Robert et al. |
| 7,731,891 B2 | 6/2010 | Cooper |
| 2002/0180124 A1 | 12/2002 | Kitamura et al. |

FOREIGN PATENT DOCUMENTS

| | | |
|---|---|---|
| DE | 25 46 647 A1 | 5/1976 |
| GB | 934112 A | 8/1963 |

LANCE AND METHOD FOR DETERMINING REACTION DATA OF THE COURSE OF A REACTION

CROSS REFERENCE TO RELATED APPLICATIONS

This application is divisional of and Applicant claims priority under 35 U.S.C. §§ 120 and 121 of U.S. patent application Ser. No. 14/779,615 filed on Sep. 24, 2015, which application is the National Stage of PCT/AT2014/050074 filed on Mar. 25, 2014, which claims priority under 35 U.S.C. § 119 of Austrian Application No. A 50204/2013 filed on Mar. 25, 2013, the disclosures of which are incorporated by reference. A certified copy of priority Austrian Patent Application No. A 50204/2013 is contained in parent U.S. application Ser. No. 14/779,615. The international application under PCT article 21(2) was not published in English.

BACKGROUND OF THE INVENTION

1. Field of the Invention

The invention relates to a lance and a method for the determination of reaction data of a reaction sequence, in which a reaction gas is top-blown by means of at least one lance onto a metallic melt in a metallurgical vessel and simultaneously measured data are recorded, as a function of which reaction data about the reaction sequence are determined, wherein the lance for the recording of measured data blows out a gas being conveyed separately from the reaction gas via at least one outlet opening of at least one measuring line.

2. Description of the Related Art

In order to be able to monitor or control a reaction sequence of a top-blowing process or oxygen-top-blowing process, it is known from the prior art (DE 1290557 A1) to measure the electrical conductivity between the lance and the metallurgical vessel during the reaction sequence. By means of these recorded measured data, the reaction sequence is interpreted or reaction data about the reaction sequence are determined therewith. In particular, supposedly overfoaming of the foamed slag, which is formed during the top-blowing of oxygen at a high flow velocity onto the melt in the metallurgical vessel, is also detected therewith and subsequently the danger of a slopping is reduced. However, the measured electrical conductivity is dependent on a large number of reaction parameters of the reaction sequence, and so the danger of an overfoaming can be detected only poorly reliably by means of such methods. Furthermore, metallurgical changes in the reaction sequence are manifested relatively sluggishly in the electrical conductivity, thus making a dynamic determination of reaction data about the reaction sequence difficult.

Moreover, a method for the determination of the depth of immersion of a lance in a metallic melt is known from DE 2239216 A1. For this purpose, a pressurized gas being conveyed separately from the reaction gas of the lance is blown out at the bottom end of the lance via a measuring line of the lance. Measured data about the pressure differences between an ambient pressure and the pressure at the bottom end of the lance are used for the determination of the depth of immersion of the lance. Disadvantageously, extremely violent chemical reactions of the reaction gas with the melt can be expected during the measurement, which falsifies the recording of measured data and thus may jeopardize the stability of the process.

In addition, for the measurement of the height of a foamed slag in a metallurgical vessel, it is known (U.S. Pat. No. 4,359,211 B) to inject pressurized gas through the wall of the metallurgical vessel at different heights. Such a measuring device needs a relatively complex structural change of the metallurgical vessel in order to be able to assure its leak-tightness at all times against escape of metallurgical melt despite wall openings.

SUMMARY OF THE INVENTION

The task of the invention is therefore, starting from the prior art depicted initially, to provide a method that can determine the reaction data of a metallurgical reaction sequence rapidly and reliably. In addition, it is intended that the method will be simple and resistant to metallurgical processes.

The invention accomplishes the stated task by the fact that the lance for the recording of measured data blows out the gas being conveyed separately from the reaction gas laterally via at least one outlet opening of at least one measuring line, wherein the internal pressure of at least one gas bubble formed at this outlet opening of the respective measuring line is measured.

If the lance for the recording of measured data blows out the gas being conveyed separately from the reaction gas laterally via at least one outlet opening of at least one measuring line, wherein the internal pressure of at least one gas bubble formed at this outlet opening of the respective measuring line is measured, measured data can be recorded rapidly and reliably. As a function thereof, reaction data about the reaction sequence can be determined subsequently. In particular, a pressure measurement at the measuring line with an outlet opening discharging alongside the lance can be performed relatively easily and, by virtue of the circumstance of a direct interaction of the gas bubble with the melt or with its foamed slag, can also be achieved with extremely fast response, which may entail numerous advantages—including with respect to the process safety. In addition, such a pressure measurement can be performed sufficiently far removed from the loads caused by the reaction sequence, which may permit an extremely stable and precise process with reproducible results.

In general, it is pointed out that oxygen can be excellent as the reaction gas.

In order to increase the accuracy of measurement of the reaction data further, it may be provided that the lance blows gas out laterally via at least two measuring lines, wherein reaction data about the reaction sequence are determined as a function of an establishment of the difference between the measured internal pressures of the gas bubbles. By means of this establishment of a difference, even small changes in the metallurgical reaction sequence can be measured, and so metallurgical processes can be recorded particularly rapidly by means of the method according to the invention.

If the measuring lines discharging at the same lance height form gas bubbles differing in size from one another, not only is it possible to record measured pressure data suitable for establishment of a difference, but in addition these measured pressure data may also contribute to the increase of the accuracy of the reaction data. In particular, by virtue of the measuring lines discharging at the same lance height, it is possible, among other things, to suppress disturbances acting on both measurements and to generate measured data with increased signal-to-noise ratio.

However, it is also conceivable that measuring lines discharging at different lance heights form equally large gas bubbles. In particular, by plotting of gas bubbles at difference lance heights, it is possible with methodical reliability to infer a filling level height of the foamed slag in the vessel.

An increased measurement accuracy can be achieved when measuring lines discharging at different lance heights form gas bubbles of different size.

The mutual influence of the measuring lines can be considerably reduced when the measuring lines blow out gas on opposite sides on the lance body. In this way a further increased measurement accuracy can be expected. This may be particularly advantageous when the measuring lines blow out gas diametrically oppositely on the lance body.

If the measuring line or the measuring lines is or are simultaneously cooled by the cooling medium that cools the lance, steady conditions of the gas discharge can be achieved. In this way an improved reproducibility of the method can be established.

The method according to the invention can be particularly advantageous by the fact that reaction data, on the basis of which the reaction sequence of a top-blowing process can be controlled or adjusted, are determined therewith. For example, it is possible in this way to detect a slopping in timely manner and thus to reduce the danger of a slopping or to initiate countermeasures in this regard.

A further task of the invention is to provide, for top-blowing a reaction gas onto a metallic melt disposed in a metallurgical vessel, a structurally simple and robust lance with which measured data can be obtained rapidly and reproducibly in order to be able to determine reaction data about the reaction sequence.

The invention accomplishes the task with respect to the lance by the fact that the measuring line in at least one outlet opening ends laterally at the lance jacket of the lance body and is formed for the generation of at least one gas bubble.

If the measuring line ends in at least one outlet opening laterally at the lance jacket of the lance body, this opening disposed alongside on the lance jacket can be used to record measured data relatively far removed from the top-blowing region. Thus the measurement can be performed in a manner that is relatively insensitive to the turbulent flows occurring in this lower zone of the lance. In particular, when this outlet opening is formed for the generation of at least one gas bubble and a relatively disturbance-free zone is needed for the streaming of gas bubbles into the melt or foamed slag in order to record rapid and accurate measured data about the reaction sequence. In this way, for example, the danger of an undesired slopping can also be reduced by means of the lance according to the invention, or suitable countermeasures can be initiated in timely manner therewith. In addition, a reliable early detection of a disadvantageous slopping is possible in this way.

Advantageously these measured data can be determined via the lance relatively far removed from the loads caused by the reaction sequence when a measuring device is provided that contains, for the recording of measured data, a sensor, which is in communication with the measuring line for the recording of measured data dependent on the internal pressure of the gas bubble.

A difference measurement can be permitted when the lance body contains at least two measuring lines, which discharge laterally on the lance body.

For such a difference measurement, it may be sufficient when the outlet openings of the measuring lines have different outlet cross sections. In this regard the measuring lines may even discharge at the same height on the lance body.

Alternatively, it is also conceivable that the outlet openings of the measuring lines discharge laterally at different heights on the lance jacket. In addition, this in combination with different outlet cross sections may achieve an increased sensitivity. In this way the accuracy of the measured data can be increased.

The mutual influence of the measuring lines may be reduced when their outlet openings discharge on opposite sides on the lance body. In this way, not only can the measurement accuracy be further increased but also the construction complexity can be reduced therewith, especially in regard to the cooling of the lance. In particular, it may be excellent for this purpose when the outlet openings discharge diametrically oppositely on the lance body.

The temperature at the bubbling opening of the measuring line may be stabilized when the measuring line is in thermally conducting communication, at least zonally, with the cooled lance jacket of the lance body. In this way an increased measurement accuracy can be achieved.

BRIEF DESCRIPTION OF THE DRAWINGS

As an example, the subject matter of the invention is illustrated in more detail on the basis of an alternative embodiment in the figures, wherein.

DETAILED DESCRIPTION OF PREFERRED EMBODIMENTS

Figure 1:
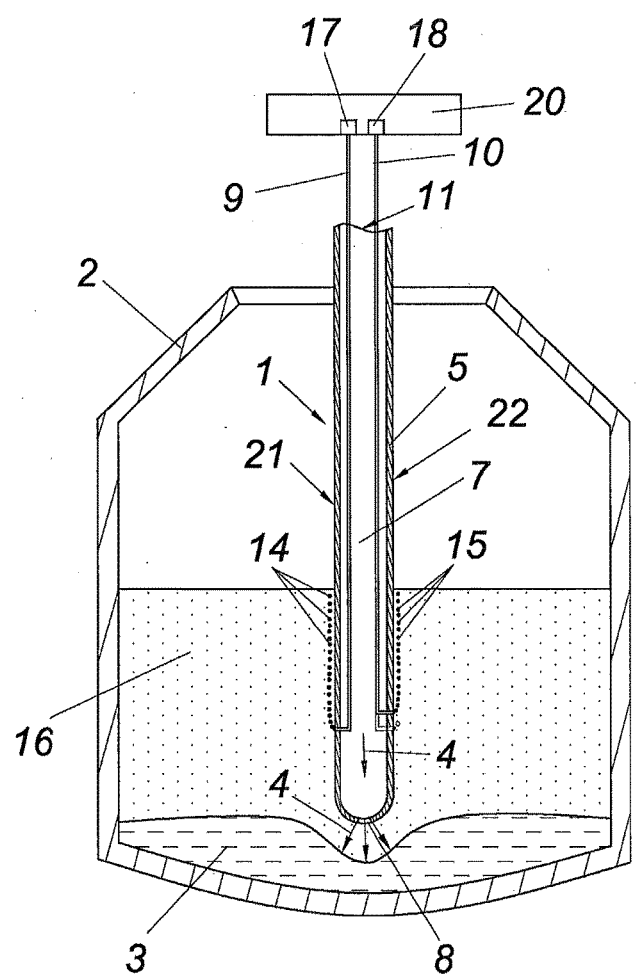
FIG. 1 shows a cutaway side view of a device for the determination of reaction data and FIG. 2 shows a detail view of FIG. 1.

According to FIG. 1, a lance 1 is illustrated that is dipped into a metallurgical vessel 2, which contains a metallic melt 3, for example a ferrous material, an aluminum material, a metallic alloy or the like. The lance 1 is used to top-blow a reaction gas 4 onto the melt 3, in order to set a metallurgical reaction sequence in motion in this way. Such a reaction sequence may be, for example, a refining of pig iron with oxygen, which is known as the LD process. To be able to withstand the loads caused by the reaction sequence, the lance 1 is equipped with a cooled outer lance jacket 5. Such a cooling may be created, for example, by a double-walled construction of the lance jacket 5 that conveys water as coolant, although for clarity this is not further illustrated in the drawings. The gas supply 7 of the reaction gas 4 of the lance 1 is discharged in the bottom end of the lance 1 via an opening 8 or a plurality of openings, not illustrated in more detail, of the lance jacket 5, and flows onto the melt 3. It goes without saying that any opening shape or number of openings 8 is conceivable.

The lance 1 has at least one—in the specific exemplary embodiment two measuring lines 9 and 10—which is provided in the lance body 11 in a manner protected from the influences of the top-blowing process. According to the invention, these measuring lines 9 and 10 discharge in at least one outlet opening. In the example, two outlet openings 12 and 13 are provided on the lance jacket 5, disposed laterally or alongside, of the lance body 11. The outlet openings 12 and 13—constructed as bubbling openings—generate gas bubbles 14 and 15, which can be seen better in FIG. 2. These gas bubbles 14 and 15 stream into the foamed slag 16, which is formed above the melt 3 as a result of the metallurgical reaction sequence. With a measuring line 20, which with sensors 17 and 18 records measured data about the respective pressure of measuring lines 9 and 10 and thus also about the internal pressure of the gas bubbles 14 and 15 at the respective outlet opening 12 and 13, it is now possible to infer reaction data of the reaction sequence or to determine these therewith accurately and rapidly. Thus a slopping, which is known to be undesirable in top-blowing processes, can be detected in timely manner—subsequently the top-blowing process is advantageously adjustable and controllable on the basis of the reaction data recorded in this way.

Since two measuring lines 9, 10 are provided in the lance body 11, the measurement or the determination of the reaction data can be undertaken considerably more accurately by a measurement of the difference between their internal pressures. Such difference measurements are known, for example, in "gas blowing processes" of the prior art.

In order to ensure the establishment of a sufficiently large difference, the outlet openings 12 and 13 of the two measuring lines 9 and 10 end at different heights laterally on the lance jacket 5.

Figure 2:
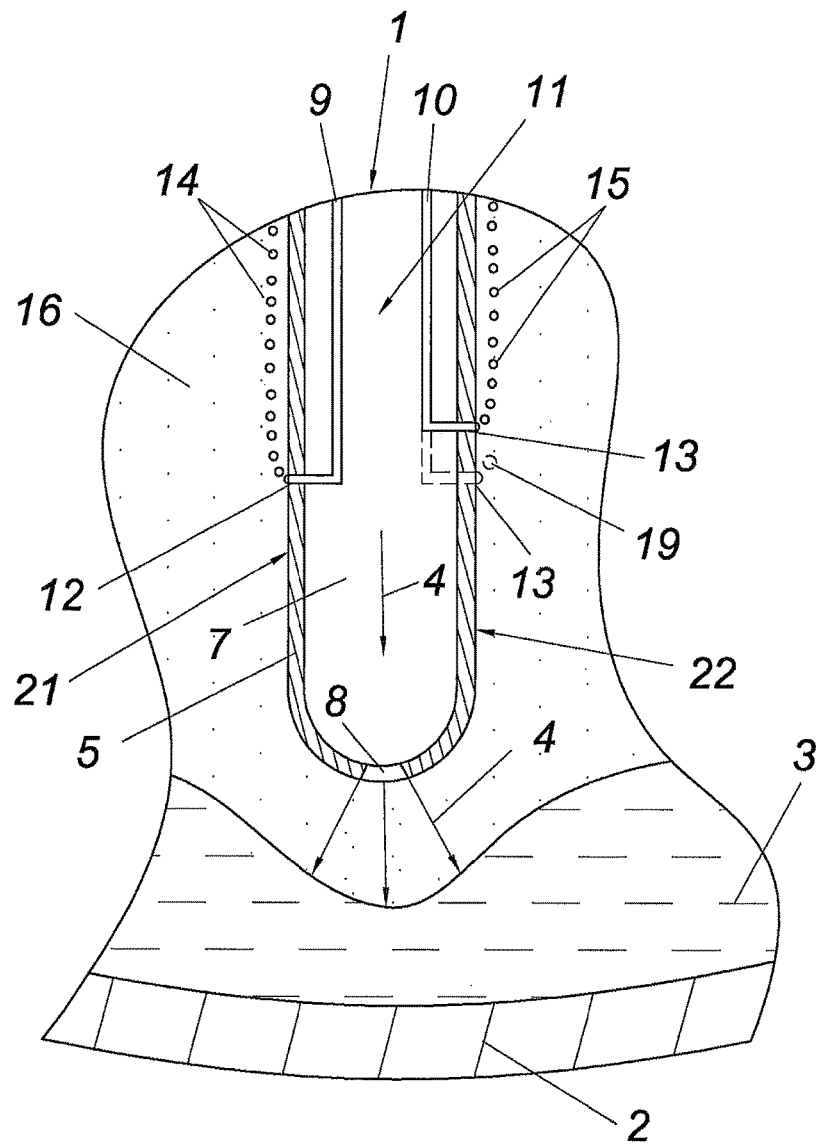

As can be seen in particular in FIG. 2, it is also conceivable that these outlet openings 12, 13 discharge laterally at the same height on the lance jacket 5 and have different outlet cross sections, in order to generate gas bubbles 14 and 19 of different size in this way.

It goes without saying that a combination of different heights of the outlet openings 12, 13 with various outlet cross sections is conceivable. However, this is not illustrated in more detail.

In addition, the measuring lines 9 and 10 are in thermally conducting communication in their outlet zones with the cooled lance jacket 5, in order to cool these measuring lines 9 and 10 simultaneously with the lance jacket 5 and thus to ensure reproducible process conditions for the bubbling of gas 14, 15, 19 into the foamed slag 16.

Advantageously, it is further provided that the outlet cross sections 12, 13 of the measuring lines 9, 10 discharge on opposite sides 21, 22 on the lance body 11. In this way the bubbling of gas 14, 15, 19 is highly independent of one another—especially when the outlet openings 12, 13 of the measuring lines 9, 10 are disposed diametrically oppositely on the lance body 11. Thereby the measurement accuracy is considerably improved.

In general, it is pointed out that—as may be inferred from FIGS. 1 and 2—the measuring lines 12, 13 discharge respectively on different sides 21, 22 or alongside the lance body 11, although this does not necessarily have to be the case. In addition, a combination of different heights of the outlet openings 12, 13 with various outlet cross sections is also conceivable here—although this is not illustrated in more detail.

What is claimed is:

1. A method comprising:
    (a) top-blowing a reaction gas using at least one lance onto a metallic melt in a metallurgical vessel and
    (b) simultaneously recording measured data, and
    (c) determining reaction data about reaction sequence as a function of the measured data so recorded,
    wherein the at least one lance blows out a gas being conveyed separately from the reaction gas via at least one outlet opening of at least one measuring line,
    wherein the at least one lance blows out the gas being conveyed separately from the reaction gas laterally via the at least one outlet opening of the at least one measuring line, and
    wherein an internal pressure of at least one gas bubble formed at the at least one outlet opening of the respective at least one measuring line is measured to provide the measured data.

2. The method according to claim 1, wherein the at least one lance blows the gas out laterally via at least first and second measuring lines into first and second sets of gas bubbles, wherein the reaction data about the reaction sequence are determined as a function of an establishment of the difference between measured internal pressures of the gas bubbles of the first set of gas bubbles and the second set of gas bubbles.

3. The method according to claim 2, wherein the first and second measuring lines discharge the first and second set of gas bubbles at an identical lance height and wherein the gas bubbles of the first set of gas bubbles differ in size from the gas bubbles of the second set of gas bubbles.

4. The method according to claim 2, wherein the first and second measuring lines discharge the first and second set of gas bubbles at different lance heights and wherein the gas bubbles of the first and second set of gas bubbles have equal size.

5. The method according to claim 2, wherein the first and second measuring lines discharge the first and second set of gas bubbles at different lance heights and wherein the gas bubbles of the first set of gas bubbles have a different size from the gas bubbles of the second set of gas bubbles.

6. The method according to claim 2, wherein the lance body has a first side and a second side opposite the first side and the first and second measuring lines blow out the gas on the first and second sides, respectively.

7. The method according to claim 1, wherein the at least one measuring line is simultaneously cooled by a cooling medium that cools the lance.

8. The method according to claim 1, further comprising controlling or adjusting the reaction sequence based on the reaction data determined.

* * * * *

UNITED STATES PATENT AND TRADEMARK OFFICE
CERTIFICATE OF CORRECTION

PATENT NO. : 10,126,286 B2
APPLICATION NO. : 15/613417
DATED : November 13, 2018
INVENTOR(S) : Schuster et al.

Page 1 of 1

It is certified that error appears in the above-identified patent and that said Letters Patent is hereby corrected as shown below:

In the Claims

In Column 6, Lines 16-17, (Lines 15-16 of Claim 1) please delete the word "respective".

Signed and Sealed this
Twenty-fifth Day of December, 2018

Andrei Iancu
*Director of the United States Patent and Trademark Office*